United States Patent [19]

Primes et al.

[11] Patent Number: 4,582,705
[45] Date of Patent: Apr. 15, 1986

[54] COMPOSITION FOR DETOXIFICATION

[76] Inventors: Leonard Primes, 230 Juniper Cir. No., Lawrence, N.Y. 11559; Thomas Young, 5 Beach 119th St., Rockaway Point, N.Y. 11694

[21] Appl. No.: 575,537

[22] Filed: Apr. 26, 1984

Related U.S. Application Data

[63] Continuation of Ser. No. 397,420, Jul. 12, 1982, abandoned.

[51] Int. Cl.$^4$ .................... A61U 31/34; A61U 33/06; A61U 33/20; A61U 33/30; A61U 33,34
[52] U.S. Cl. .................... 424/141; 424/145; 424/149; 424/153; 424/154; 514/474
[58] Field of Search ............... 424/149, 153, 154, 145, 424/141; 514/474

[56] References Cited

U.S. PATENT DOCUMENTS 4,167,564  9/1979  Jensen ................................ 424/177
4,322,407  3/1982  Ko ..................................... 424/128

*Primary Examiner*—Stanley J. Friedman
*Attorney, Agent, or Firm*—Evelyn M. Sommer

[57] ABSTRACT

Compositions for use in and a method for detoxifying chronic alcoholics and hard-line drug addicts while avoiding all of the major symptoms associated with alcohol and/or drug withdrawal, which comprises administering orally to such a subject an effective amount of a formulation in dosage unit form having the following composition:

- 5-50 grams of at least one magnesium salt selected from the group consisting of magnesium chloride, magnesium sulfate, magnesium citrate and other suitable magnesium salts;
- 500 mgms. to 2 grams of at least one potassium salt selected from the group consisting of potassium citrate, potassium sulfate, potassium chloride, potassium bromide, potassium bitartrate and other suitable potassium salts; and
- 50 mgms. to 5 grams of at least one salt selected from the group consisting of the citrates, ascorbates, chlorides, bromides, sulfates, carbonates, gluconates, lactates and bitartrates of calcium, sodium, zinc, copper and lithium. The compositions can additionally contain vitamins, particularly the B vitamins, nutrients, sugars, flavoring and coloring agents, and are provided in powder form. Just prior to use, the compositions are introduced into a suitable diluent, preferably water in an amount suitable for dissolving all of the powder and for being administered as a single dosage unit or may be provided for administration in the form of a prepared liquid.

14 Claims, No Drawings

COMPOSITION FOR DETOXIFICATION

This is a continuation of application Ser. No. 397,420, filed July 12, 1982, now abandoned.

The present invention relates to therapeutic compositions and more particularly to therapeutic compositions adapted specifically for use in detoxifying chronic alcoholics and hard-line drug addicts while avoiding all of the major symptoms associated with alcohol and/or drug withdrawal.

According to a recent report of the Metropolitan Life Insurance Company, there are in the United States four million people who are alcoholics. Sometimes it appears that most estimates, including the one just noted have been made considering only the overt habitues of the skid rows. Physicians however, are aware of another group of alcoholic which have been designated as hidden alcoholics. These are the individuals who drink surreptitiously and manage to keep their habituation secret. Many of these people enjoy some occupational stability and some are engaged in top level positions. It is estimated that only 6% of the alcoholic population is receiving treatment for the disease as such.

The following steps have been suggested in the treatment of acute alcoholism or drunkenness:
1. Remove the liquor from the patient.
2. Get the alcohol out of the stomach and tissues.
3. Administer fluids and food to assist in restoration of water balance, vitamins and salts. For this purpose, it is proposed that 1-2 liters of 10% dextrines in isotonic salt solution be injected slowly intraveneously. To this fluid there is added 25 units of insulin and 100 to 200 mgms. of thiamine hydrochloride.
4. Reduce the blood levels of the alcoholic. This has been accomplished from the use of intraveneous injections of triiodothyronine. For reducing the blood levels of alcohol in acutely intoxicated persons, there is injected a total dosage of 200 mcg. of the hormone. A sobering effect occurs due to the accelerated alcohol metabolism.
5. Administer sedatives when indicated. For the purpose of sedation 60-120 mgms. of phenobarbital is administed as an anti-convulsant, 180 mgms. of diphenylhydantoin sodium may be desirable. This treatment has to be continued for several hours.
6. Protect the patient so that he cannot injure himself or others. (See below for treatment of delirium tremens.)

The treatment of the chronic alcoholic has heretofore been undertaken along the following lines:
1. Drug therapy
2. Nutritional therapy
3. Psychotherapy As drug therapy, thiamine hydrochloride 100 to 300 mgms. intraveneously is used. The barbiturates such as pentobarbital sodium, 100 to 200 mgms. are administered. Diphenylhydantoin sodium, 100 to 200 mgms. is used to combat convulsive seizures. Dextro-amphetamine (Dexedrin sulfate) 5-50 mgms. 3 times a day is also used in depressed alcoholics.

Dietary measures are instituted using a diet with a high caloric intake supplemented by vitamins, especially thiamine hydrochloride.

For treatment of delirium tremens, alcoholics' mental disease, characterized by visual hallucinations and accompanied by marked fear of the objects seen, confusion, disorientation for time, place and in general being out of contact or off the beam, the following steps have been suggested:
1. Withdraw alcohol abruptly.
2. Give 100 mgms. each of phenobarbital and diphenylhydantoin sodium orally as a sedative and anticonvulsant for several days.
3. Inject 1-2 liters of 10% dextrose in normal salt solution intraveneously.
4. Administer by slow intraveneous drip 100 to 200 mgms. of thiamine hydrochloride and 25 units of insulin.

Administer psychotropic drugs such as chlorpromazine, promazine and meprobromate. In the depressions that frequently are associated with the withdrawal of alcohol, d-amphetamines may be used to elevate the patient's mood. Monitoring for hypotension and other side effects of these drugs and from their synergism with alcohol must be carried out and also habituation to the psychotropic drugs must be avoided.

The chronic alcoholic usually shows a distorted electrolyte balance. Thus, in connection with alcohol withdrawal, fluid and electrolyte therapy has received special attention.

Low serum potassium levels are commonly seen in withdrawal and may reflect total body potassium depletion. Hyperventilation may contribute to hypokalemia by causing extracellular to intracellular potassium shifts. Thus, an assessment of serum potassium as a guide to potassium requirements must be made.

It has been proposed that for each change in blood pH of 0.1 unit, the serum potassium is adjusted 0.6 mEq/L in the opposite direction. The rate of administration is critical since potassium can cause cardiac arrhythmias.

Statistics have shown most alcoholics to be magnesium depleted regardless of their serum levels. This deficiency may be 1-2 mEq/kg of body weight. Diminished dietary intake, vomiting and an ethanol-medicated increase in urinary magnesium output are believed to contribute to this deficiency.

Magnesium replacement therapy has been proposed and specifically 2 g $MgSO_4$ (8 mEq/g) has been used.

In addition, for the seizures and fevers accompanying alcohol withdrawal which are in part precipitated by hyperventilation and respiratory alkalosis during the early period of abstinence it has been proposed that benzodiazepine therapy and magnesium replacement 1 to 2 grams magnesium sulfate intraveneously can be helpful in preventing such symptoms. If seizures do occur, intraveneous diazepines are used.

This use of magnesium and particularly magnesium sulfate for producing the characteristic actions of magnesium ion and specifically for its systemic action as an anticonvulsant is known as is its use for this purpose in connection with the muscular tremors or delirium observed in alcoholics. For alleviating such magnesium deficiency it has been recommended that there be given intramuscular injections of 2 grams of magnesium sulfate, as a 50% solution, 4 times daily for several days.

In U.S. Pat. No. 3,829,569 a therapeutic composition for combatting the major symptoms resulting from the overindulgence of alcoholic beverages has been disclosed comprising a two-part formulation, one part of which contains aspirin and aluminum hydroxide and the other part of which contains magnesium carbonate, magnesium trisilicate, nicotinamide, thiamine hydrochloride and peppermint oil and either or both of which contain caffeine. In this preparation, the magnesium trisilicate and magnesium carbonate are both present as antacids. From the general formulation, it is apparent that the preparation disclosed in a "hangover remedy" and that there is no concern with adjustment of magnesium deficiency such as is found in the chronic alcoholic.

In summary, in all of the proposals advanced heretofore which recognize an electrolyte imbalance in the alcoholic and even in those case which suggest the use of magnesium carbonate and magnesium trisilicate as an antacid, there is no suggestion to administer the magnesium compound in an amount contemplated by the applicant herein, of from 5 up to 50 grams per individual dose. Further, it has not been recognized that for achieving the desired detoxification without concomitant withdrawal symptoms the other abnormal electrolyte levels have to be restored to normal levels and specifically this is true of the potassium levels if the detoxification is to be satisfactorily achieved.

It has now been found by the applicant that the administration of megadoses of the essential electrolytes results in the substantial immediate restoration of the electrolyte levels of body fluids.

More specifically, the applicant has found that the administration of magnesium in megadoses together with other electolytes such as potassium, calcium, sodium, copper, zinc, lithium and others has a synergistic effect resulting in a marked improvement in the detoxification of the acute and chronic alcoholic and the drug addict as well.

The detoxification in accordance with the invention is completed in 24 to 72 hours without any of the usually-encountered withdrawal effects.

In accordance with the invention, compositions for use in and a method for detoxifying chronic alcoholics and hard-line drug addicts while avoiding all of the major symptoms associated with alcohol and/or drug withdrawal are now proposed. The method comprises administering orally to such a subject an effective amount of a formulation in dosage unit form having the following composition:

5–50 grams of at least one magnesium salt selected from the group consisting of magnesium chloride, magnesium sulfate and magnesium citrate;

500 milligrams to 2 grams of at least one potassium salt selected from the group consisting of potassium citrate, potassium sulfate, potassium chloride, potassium bromide and potassium bitartrate; and 50 milligrams to 5 grams of at least one salt selected from the group consisting of the citrates, ascorbates, chlorides, bromides, sulfates, carbonates, gluconates, lactates and bitartrates of calcium, sodium, zinc, copper and lithium. The compositions can additionally contain vitamins, particularly the B vitamins, sugar, flavoring and coloring agents and are provided in power form.

The compositions are administered in the form of a prepared liquid or just prior to use, are introduced into a suitable diluent, preferably water in an amount suitable for dissolving all of the powder form components and for being readily administered as a single dosage unit These compositions which are new, are administered orally in the form of their solutions in water. Preferably the solutions are taken under medical supervision. They are prepared by dissolving the dry powder mixture in up to about 300 mls. of water. If the patient cannot or will not drink the preparation, the composition can be administered via a stomach tube. It is also possible to administer the solutions parenterally but in this connection the formulations must be specifically prepared for that type of administration.

The salt contents as set out herein are calculated for a single dose. It can be appreciated that the powdery mixture can be made up in batches and aliquots to provide the desired quantities, i.e., single dosage unit then taken from the master batch. Each single dose is intended to be administered to the subject two to three times daily for from one to three days.

The general formulation of the compositions of the invention can be seen from the following (the recited vitamins, flavoring agents, coloring agents, etc. are not critical but only preferred for improving the formulation):

5 to 50 grams total of magnesium chloride, magnesium sulfate, magnesium citrate or the like.

500 mgms. to 2 grams total of potassium citrate, potassium sulfate, potassium chloride, potassium bromide, potassium bitartrate and the like.

50 mgms. to 5 grams total of at least one of calcium ascorbate, calcium pantothenate, calcium carbonate, calcium lactate, sodium chloride, sodium ascorbate, sodium sulfate, sodium citrate, zinc gluconate, zinc chloride, zinc sulfate and the like. Copper and lithium salts may also be present but in this case in the indicated pharmaceutical ranges.

10 to 150 mgms. thiamine mononitrate (Vitamin $B_1$).

1 to 20 mgms. riboflavin phosphate (Vitamin $B_2$ phosphate).

1 to 250 mgms. pyridoxine hydrochloride (Vitamin $B_6$).

50 to 100 mgms. niacinamide (Vitamin $B_3$).

5 to 100 mgms. panthenol (Vitamin $B_5$).

Sugar, flavoring agents such as peppermint oil, licorice, cherry, orange, grape and the like and coloring agents such as are conventionally used in pharmaceutical preparations.

This invention will appear more fully from the examples which follow. These examples are set forth by way of illustration only, and it will be understood that the invention is not to be construed as limited in spirit or in scope by the details contained therein.

EXAMPLE 1

A formulation particularly suitable for use in detoxifying an alcoholic without onset of withdrawal symptoms is prepared by intimately admixing the following:

Magnesium sulfate: 10 gms.
Potassium citrate: 500 mgms.
Calcium ascorbate: 1 gm.
Sodium chloride: 100 mgms.

The dry mixture is prior to use dissolved in up to 250 ml. water. If desired a flavorant such as vanillin, cherry or mint can be added.

This solution is administered orally to the alcoholic as a single dose two or three times daily for from one to three days.

EXAMPLE 2

A mixture of
Magnesium sulfate: 50 gms.
Potassium sulfate: 2 gms.
Sodium ascorbate: 2 gms.
Calcium pantothenate: 500 mgms.
was prepared.

Prior to use in the treatment of an acute alcoholic or hard line drug addict, the dry preparation can be converted to a liquid dosage form.

EXAMPLE 3

The following ingredients were combined to provide a formulation suitable for use in detoxifying an alcoholic or drug addict using only two (2) to nine (9) doses:
 Magnesium sulfate: 25 gms.
 Potassium chloride: 1 gm.
 Calcium carbonate: 5 gms.
 Sodium sulfate: 1 gm.

Just prior to use, a flavorant such as peppermint oil and/or sugar can be added along with sufficient water to make up to 200 ml. of a liquid dosage form.

EXAMPLE 4

A powder formulation was prepared from the following:
 Magnesium citrate: 30 gms.
 Potassium citrate: 500 mgms.
 Calcium ascorbate: 1 gm.
 Sodium ascorbate: 500 mgms.
 Zinc sulfate: 50 mgms.
 Thiamine mononitrate: 100 mgms.
 Riboflavin: 10 mgms.
 Pyridoxine HCl: 50 mgms.

EXAMPLE 5

A formulation in accordance with the invention was prepared by mixing together in the amounts indicated:
 Magnesium citrate: 50 gms.
 Calcium ascorbate: 1 gm.
 Potassium sulfate: 1 gm.
 Zinc chloride: 100 mgms.
 Sodium citrate: 100 mgms.

The resuting dry mixture was introduced into 200 ml. water and stirred until dissolved. 100 grams of sugar and 5 mg. of a flavorant such as licorice were then added under stirring. The solution thereby retained was suitable for use as a single dosage unit for oral administration.

EXAMPLE 6

A mixture was prepared from the following dry ingredients:
 Magnesium sulfate: 25 gms.
 Calcium lactate:

A mixture was prepared from the following dry ingredients:
 Magnesium sulfate: 25 gms.
 Calcium lactate: 2 gms.
 Potassium citrate: 200 mgms.
 Sodium ascorbate: 500 mgms.

This power formulation in liquid oral dosage form was suitable for use in the detoxification of alcoholics and hard line drug addicts.

EXAMPLE 7

The following dry ingredients were combined to form a therapeutic composition to be taken orally as a single dose:
 Magnesium chloride: 50 gms.
 Calcium lactate: 5 gms.
 Potassium bitartrate: 1 gm.
 Sodium chloride: 500 mgms.

EXAMPLE 8

The following specific ingredients in the quantities recited were combined to prepare a composition for providing the therapeutic effects described above:
 Magnesium sulfate: 50 gms.
 Potassium bromide: 500 mgms.
 Calcium ascorbate: 2 gms.
 Zinc gluconate: 50 mgms.

EXAMPLE 9

A powder mixture of the following ingredients was prepared:
 Magnesium sulfate: 50 gms.
 Potassium citrate: 1 gm.
 Sodium citrate: 500 mgms.
 Calcium lactate: 5 gms.
 Zinc sulfate: 100 mgms.
 Thiamine mononitrate: 200 mgms.
 Riboflavin 5 phosphate: 50 mgms.
 Pyridoxine HCl: 100 mgms.
 Niacinamide: 100 mgms.
 Panthenol: 100 mgms.
 Cyanocobalamine: 20 micrograms
 Sugar: 125 gms.

The powder mixture was dissolved in sufficient water to form 300 ml. of solution.

Cherry flavor and a pharmaceutically acceptable red colorant were then added.

This single dosage preparation was administered twice a day for three days under supervision of medical personnel and was entirely effective for detoxifying an alcoholic, no withdrawal symptoms being observed.

EXAMPLE 10

The procedure of Example 9 was repeated using the following ingredients in the amounts shown:
 Magnesium sulfate: 10 gms.
 Calcium ascorbate: 1 gm.
 Potassium chloride: 100 mgms.
 Zinc sulfate: 50 mgms.
 Sugar: 100 gms.
 Water to: 250 ml.
 Grape flavorant and suitable colorant.

This single dosage preparation was administered two to three times a day for two days and was an effective formulation for detoxifying an alcoholic and for providing the maximum therapeutic benefit without any evidence of withdrawal symptoms.

Accordingly, the compositions of the invention which provide the essential electrolytes and specifically megadoses of magnesium together with other electrolytes such as potassium, calcium, sodium, copper, lithium, zinc and the like, can be used to detoxify alcoholics and drug addicts by restoring the electrolyte levels from their depleted state to normal without any of the attendant severe withdrawal symptoms usually associated with such detoxification.

In its method of use aspect, this invention relates to the treatment of alcoholics and hard-line drug addicts for the purpose of restoring to normal the electrolyte levels of the body fluids thereby avoiding withdrawal symptoms. Results of experiments indicate that the composition administered two to three times daily for a period of one to three days are effective in the treatment of chronic alcoholics and hard-line drug addicts while substantially lessening, i.e., eliminating the otherwise behavioral and physiological changes observed in such subjects during detoxification and being attributable to loss of magnesium and potassium levels in their body fluids.

In medical practice, the compositions according to the present invention can be administered orally and also parenterally. Oral administration is preferred and has been described above. It is understood however that the compositions can be made up for parenteral administration, using a suitable liquid diluent capable of dissolving all of the ingredients, with precautions, including sterilization being taken vis-a-vis such method of administration. In either case, the magnesium is supplied so as to provide the same in a mega amount, the other electrolytes being supplied in an amount effective to restore the same to their normal physiological levels.

The formulation of the medicinal agents of this invention is accomplished in the conventional manner by processing the salts, nutriments, vitamins, etc. together so as to form a dry, stable admixture.

This dry admixture is then introduced into the diluent, i.e., the water together with the flavor accelerating substance, colorant, and the like customary in galenic pharmacy and converted into the desired form for application such as solutions suitable for oral administration and flasks, glass ampules and the like suitable for parenteral administration.

What is claimed is:

1. Method for detoxifying a chronic alcoholic or hard line drug addict while avoiding all of the symptoms associated with alcohol and/or drug withdrawal which comprises administering orally to such a subject a composition in dosage unit form comprising:
   5-50 grams of at least one magnesium salt selected from the group consisting of magnesium chloride, magnesium sulfate and magnesium citrate;
   50 milligrams 2 grams of at least one potassium salt selected from the group consisting of potassium citrate, potassium sulfate, potassium chloride, potassium bromide and potassium bitartrate; and
   50 milligrams to 5 grams of at least one salt selected from the group consisting of the citrates, ascorbates, chlorides, bromides, sulfates, carbonates, lactates, gluconates and bitartrates of calcium, sodium, zinc, copper and lithium.

2. Method according to claim 1, which comprises administering said composition one to three times daily for from one to three days.

3. Method for detoxifying chronic alcoholics and hard-line drug addicts while avoiding all of the major symptoms associated with alcohol and/or drug withdrawal comprising administering orally to such a subject a composition according to claim 1 in the form of its solution in water.

4. Method according to claim 3 which comprises administering such composition two to three times daily for from one to three days.

5. Method according to claim 1 wherein said composition comprises:
   Magnesium sulfate: 10 gms
   Potassium citrate: 500 mgms
   Calcium ascorbate: 1 gm
   Sodium chloride: 100 mgms.

6. Method according to claim 1 wherein said composition comprises:
   Magnesium sulfate: 50 gms
   Potassium sulfate: 2 gms
   Sodium ascorbate: 2 gms
   Calcium pantothenate: 500 mgms.

7. Method according to claim 1 wherein said composition comprises:
   Magnesium sulfate: 25 gms
   Potassium chloride: 1 gm
   Calcium carbonate: 5 gms
   Sodium sulfate: 1 gm.

8. Method according to claim 1 wherein said composition comprises:
   Magnesium citrate: 30 gms
   Potassium citrate: 500 mgms
   Calcium ascorbate: 1 gm
   Sodium ascorbate: 500 mgms
   Zinc sulfate: 50 mgms
   Thiamine mononitrate: 100 mgms
   Riboflavin: 10 mgms
   Pyridoxine HCl: 50 mgms.

9. Method according to claim 1 wherein said composition comprises:
   Magnesium citrate: 50 gms
   Calcium ascorbate: 1 gm
   Potassium sulfate: 1 gm
   Zinc chloride: 100 mgms
   Sodium citrate: 100 mgms.

10. Method according to claim 1 wherein said composition comprises:
    Magnesium sulfate: 25 gms
    Calcium lactate: 2 gms
    Potassium citrate: 200 mgms
    Sodium ascorbate: 500 mgms.

11. Method according to claim 1 wherein said composition comprises:
    Magnesium chloride: 50 gms
    Calcium lactate: 5 gms
    Potassium bitartrate: 1 gm
    Sodium chloride: 500 mgms.

12. Method according to claim 1 wherein said composition comprises:
    Magnesium sulfate: 50 gms
    Potassium bromide: 500 mgms
    Calcium ascorbate: 2 mgs
    Zinc gluconate: 50 mgms.

13. Method according to claim 1 wherein said composition comprises:
    Magnesium sulfate: 50 gms
    Potassium citrate: 1 gm
    Sodium citrate: 500 mgms
    Calcium lactate: 5 gms
    Zinc sulfate: 100 mgms
    Thiamine mononitrate: 200 mgms
    Riboflavin 5-phosphate: 50 mgms
    Pyridoxine HCl: 100 mgms
    Niacinamide: 100 mgms
    Panthenol: 100 mgms
    Cyanocobalamine: 20 micrograms
    Sugar: 125 gms
    Water q.s.: 250 mls.

14. Method according to claim 1 wherein said composition comprises:
    Magnesium sulfate: 10 gms:
    Calcium ascorbate: 1 gm:
    Potassium chloride: 100 mgms:
    Zinc sulfate: 50 mgms:
    Sugar: 100 gms.

* * * * *